United States Patent [19]
Keller et al.

[11] Patent Number: 6,048,545
[45] Date of Patent: *Apr. 11, 2000

[54] LIPOSOMAL DELIVERY BY IONTOPHORESIS

[75] Inventors: Brian C. Keller, Antioch; Daniel L. Fisher, Pleasant Hill; Stefan Kiss, Concord, all of Calif.; Michael Mezei, Halifax, Canada

[73] Assignee: BioZone Laboratories, Inc., Pittsburgh, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/681,303

[22] Filed: Jul. 22, 1996

Related U.S. Application Data

[63] Continuation of application No. 08/265,184, Jun. 24, 1994, abandoned.

[51] Int. Cl.[7] .............................. A61K 9/127; A61N 1/30
[52] U.S. Cl. .................. 424/450; 424/401; 424/1.21; 424/9.321; 424/9.51; 624/20
[58] Field of Search .................................. 424/450, 401, 424/1.21, 9.321, 9.51, 94.3; 604/20

[56] References Cited

U.S. PATENT DOCUMENTS

| | | |
|---|---|---|
| 4,340,586 | 7/1982 | Bekierkunst et al. . |
| 4,485,054 | 11/1984 | Mezei et al. . |
| 4,695,590 | 9/1987 | Lippman . |
| 4,761,288 | 8/1988 | Mezei ....................................... 424/450 |
| 4,897,269 | 1/1990 | Mezei . |
| 4,937,078 | 6/1990 | Mezei et al. . |
| 4,959,353 | 9/1990 | Brown et al. . |
| 5,064,655 | 11/1991 | Uster ....................................... 424/450 |
| 5,130,298 | 7/1992 | Cini et al. . |
| 5,160,316 | 11/1992 | Henley ....................................... 604/20 |
| 5,393,527 | 2/1995 | Malick ....................................... 435/7.1 |

OTHER PUBLICATIONS

L.P. Gangarosa et al., "Conductivity of Drugs Used for Iontophoresis," *Journal of Pharmaceutical Sciences* (Oct. 1978) 67 (10): 1439–1443.

L.P. Gangarosa et al, "Pharmacologic Management of TMJ–MPDS," *Ear, Nose, & Throat,* (1982) 61:670–678.

L.P. Gangarosa et al., "Iontophoresis (Ionto) for Pain Relief in Posterpetic Neuralgia (PHN): Doubleblind Trials," *Proc. Soc. Exper. Bio & Med.* (1986) 181 (3):476.

Praveen Tyle, "Iontophoretic Devices for Drug Delivery," *Pharm. Res.* (1986) 3 (6): 318–326.

Joanna B. Sloan et al., "Iotophoresis in Dermatology," *Jour. Am. Acad. Derm.* (Oct. 1986) 15:671–684.

Singh et al., "Transdermal Delivery of Drugs by Ionthphoresis: A review," (1989) 4:1–12.

Deleers. Res. Comm. in Chem. Pathol. & Pharmacol. 51, #1, Jan. 1986, p. 65.

*Primary Examiner*—Gollamudi S. Kishore
*Attorney, Agent, or Firm*—Morrison & Foerster LLP

[57] ABSTRACT

Substances, such as pharmaceuticals and cosmetics, are administered encapsulated within a lipid vesicle, by iontophoresis. An iontophoretic device which conforms to the contours of the body is also provided.

6 Claims, 1 Drawing Sheet

LIPOSOMAL DELIVERY BY IONTOPHORESIS

This application is a continuation of application Ser. No. 08/265,184 filed Jun. 24, 1994, now abandoned.

FIELD OF THE INVENTION

The invention relates to administration of substances, such as pharmaceuticals and cosmetics, encapsulated within a lipid vesicle, by iontophoresis.

BACKGROUND OF THE INVENTION

A variety of methods and compositions are known to administer pharmaceuticals and/or cosmetics. The controlled administration of bioactive substances, such as pharmaceuticals, has become an increasingly important mode of treatment for any diseases and disorders. Pharmaceutical manufactures have designed products to gradually release bioactive substances at a therapeutically useful rate and to spatially target the release, for example by use of a valving system, or physically as by slow diffusion. However, many of these techniques are invasive and/or cumbersome.

Iontophoresis is a technique used to enhance the penetration of topically applied drugs or other substances on skin and mucous membranes. Examples of such use include: Gangarosa et al, *J. Pharm. Sci.* (October 1979) 67(10):1439–1443 which describes the conductivity of a variety of drugs; Gangarosa et al, *Ear. Nose & Throat* (December 1982) 61:30–41 which describes a variety of drugs for the management of temporomandibular joint-myofascial pain dysfunction syndrome; Gangarosa et al., *Proc. Soc. Exper. Bio. & Med.* (1986) 181(3):476 which describes electrostatic repulsion of positively charged drugs, like pilocarpine or lidocaine, for pain relief in postherpetic neuralgia; Tyle, P., *Pharm. Res.* (1986) 3(6):318–326 which is a review of devices for iontophoresis drug delivery; Sloan et al. *J. Am. Acad. Derm.* (October 1986) 15(4,pt 1):671–684 which is a review of iontophoresis in dermatology; and Sloan et al, *Drug Design & Delivery* (1989) 4:1–12 which is a review of transdermal delivery of drugs by iontophoresis.

Iontophoresis is based on electrostatic repulsion i.e., positively charged drugs penetrate tissues more, if a positive electrode is placed on the site of application. Penetration of drugs having negative charge can be enhanced similarly with a negative electrode. Obviously the penetration of non-polar drugs cannot be infused by this type of drug delivery system. Iontophoresis has had limited utility for application of substances and has suffered from a number of disadvantages, including quantification control and the necessity to combine the active ingredient with a relatively large quantity of a carrier liquid to the area to be treated or tested.

Accordingly, there is still a need to overcome difficulties that are encountered in therapeutic or experimental administration where it is desirable to release discrete units of highly active agents, particularly in vivo, to non-invasively administer materials which are normally uncharged and to administer substances to unbroken skin which provides a proper rate of permeation without discomfort or risk of undesirable discomfort or reaction.

SUMMARY OF THE INVENTION

The present invention is directed to a method for administration to a subject of a substance encapsulated within a lipid vesicle, by iontophoresis. For example, the iontophoresis method of the invention can be used to facilitate transport of a substance in or through tissue/skin of a subject, that is in vivo (in or through the skin), ex vivo (in or through excised skin) and in vivo (in or through artificial skin).

The combination of liposomal delivery with iontophoresis is unexpectedly beneficial, because, it is non-invasive, the liposome encapsulation makes iontophoresis useful for non-polar substances and the iontophoresis improves the penetration and localization of liposome-encapsulated substance. The localization of the substance produce only a local effect, without any systemic activity, which is definitely desirable for dermal therapy.

The method of the invention can be used to obtain one or more of the following: to enhance penetration, to better control delivery, to provide a means of deeper delivery, to concentrate delivery, to localize delivery by decreasing systemic action, to target different layers of the skin for delivery, to increase the rate of delivery and the like. For example, experiments with crystal violet, basic and acid fuchsin colloidal iron, silver nitrate (used as markers) encapsulated in liposomes having positive, or negative surface charge demonstrate this. Conventional liposome anesthetic products are useful, but the lag time is usually 30 to 60 minutes. However, when charged liposome anesthetic products are used with iontophoresis, the lag time can be reduced to 5–10 minutes. The shorter lag time achieved by the iontophoresis makes the use of liposomal local anesthetics (for minor surgery or venepuncture) more practical.

By use of the method of the invention, particularly with a multiphase lipid vesicle compositions, substances can be incorporated into the subject in a concentration higher than their water or lipid solubility. Accordingly, the method using multiphase vesicle compositions is particularly useful for administering substances with low lipid or water solubility.

DETAILED DESCRIPTION OF THE INVENTION

Figure 1:
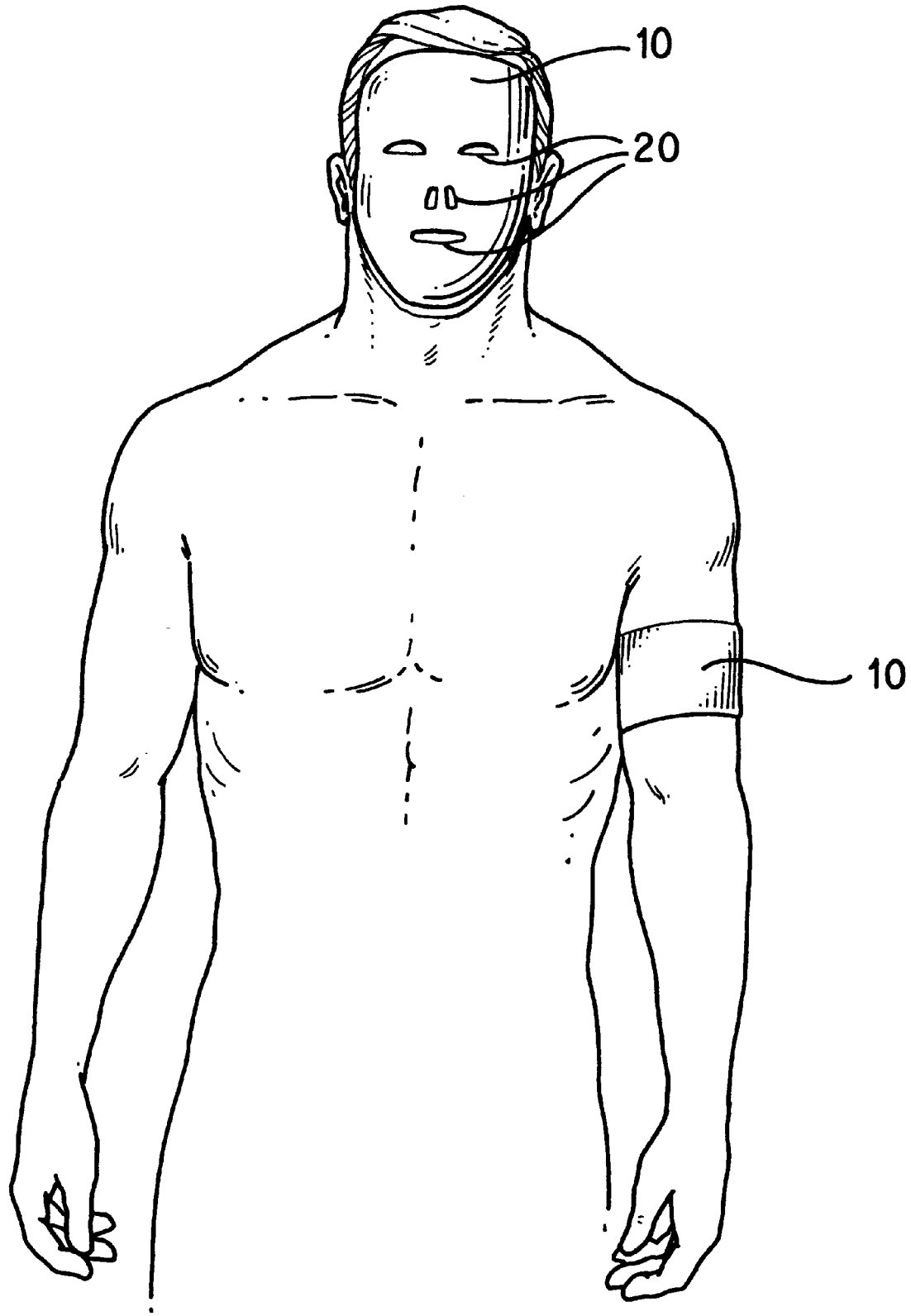
FIG. 1 is a drawing of an iontophoretic device illustrating its surface 10 conformation to the face with openings 20 for the eyes, nose and mouth or a device illustrating its surface 10 conformation to the upper arm.

Before the present method for administration of a substance is described in detail it is to be understood that the invention is not limited to the particular steps and means described, which steps and means can, of course, vary It is also to be understood that the terminology used herein is for the purpose of describing particular embodiments only, and is not intended to be limited since the scope of the present invention will be limited only by the appended claims.

It must be noted that as used in this specification and the appended claims, the singular forms of "a", "an", and "the" include plural references unless the context clearly dictates otherwise. Thus, for example, "a substance" includes mixtures of such materials, reference to "the method of iontophoresis" includes one or more methods of the general type described herein and so forth.

Unless defined otherwise all technical and scientific terms used herein have the same meaning as commonly understood by those of ordinary skill in the art to which this invention belongs. Although any methods and materials similar or equivalent to those described herein can be used in the practice of the present invention, the preferred methods and materials are now described.

All patents and publications cited herein are incorporated herein by reference for the purpose of disclosing and describing information for which the patents and publications are cited in connection with.

"Iontophoresis" as used herein means a method of treatment to drive a substance having a positive or negative charge into or through tissue/skin. Thus, iontophoresis can be used for dermal and transdermal delivery of a substance, including for diagnostic assays, forensic evaluation, delivery of a substance and the like. Accordingly, the method can be used for delivery of substances for human and veterinary use. In such case, the subject is an animal, preferably a mammal, such as cattle, rats, mice, sheep, dogs, cats, and especially is a human being.

The tissue or skin can be natural or artificial tissue and can be of plant or animal origin, such as natural or artificial skin, blood vessels, intestinal tissue and the like. The term "artificial" as used herein means as aggregation of cells of monolayer thickness or greater which are grown or cultured in vivo or in vitro and which function as a tissue but are not actually derived, or excised, from a pre-existing source or host subject.

In iontophoresis, two electrodes are placed in contact with the tissue/skin. One electrode is conveniently a pad of absorbent material soaked with the composition to be administered and a voltage is applied between the two electrodes. Usually iontophoresis is preformed with lead electrodes but other types of electrodes known in the art for iontophoresis can be used. The size and shape of the positive electrode usually corresponds to the size and shape of the area to be treated and its thickness and can readily be determined by those of skill in the art. Usually an intermediary material is contacted with the tissue/skin and the in turn is in contact with the electrodes. The intermediary material of suitable size and shape is treated with the composition to be administered usually before being placed in contact with the tissue/skin. The electrode is then placed in contact with the intermediary material. The negative electrode is placed on an optional site of dermis, again usually with an intermediary material between it and the tissue. If the neck or head is treated, iontophoresis is carried out with the current density slowly increased to the peak value desired and stopped when an unpleasant feeling is conveyed. If small electrodes are used or the composition dries out, the intermediary material can be treated periodically with the composition being administered.

Any material suitable for making contact with the tissue and the electrodes can be used as the intermediary material and usually is an absorbent material containing one or more layers such as textile, sponge, gauze, lint, paper, cotton and the like. The intermediary material can be treated with the composition in a manner conventionally known in the art, including pretreating to obtain a solid form of the substance for subsequent solution or by applying the composition immediately before or during the iontophoresis method of the invention. The intermediary material usually contains from about 0.001 to about 330, preferably about 1 to about 100 micro g of the substance to be administered within the lipid vesicle.

In the iontophoresis method of the invention, the lipid vesicle preferably have a positive or negative surface charge which enhance their penetration as a result of the electrode of the same charge as the iontophoresis unit. Because of the surface charge the penetration can be greatly increased by iontophoresis. The prolonged release rate and the reduced dispersal rate provide a controlled administration rate of the substance at or near the administration site which gives a concentrated and prolonged accuracy of action with less systemic side effects. When administered as a multiphase lipid vesicle composition, the free ionized form of the substance also penetrates better into the tissue because of the presence of the lipid vesicles which hydrate the skin.

The iontophoresis method of the invention can be conducted with conventional equipment using conventional pulse magnitude duration of the pulse and frequency of the any cycle. By way of non-limiting example, when the substance is a dye or an anesthetic, the electric current is from about 1 to about 5 milliampere, preferably, from about 1 to about 3 milliampere, and the duration is from about 1 to 15 minutes, preferably from about 5 to about 10 minutes and especially about 5 minutes.

One embodiment of the invention is directed to an iontophoretic device of FIG. 1, wherein the surface of the device 10 in contact with the tissue surface area, for example as illustrated for both the face and the upper arm, is of sufficient size and flexibility to both contact and conform to the anatomical curvature of the tissue surface. When part of the area to be within the area in contact with the iontophoretic device contains a tissue surface or area in which iontophoretic treatment is not desired, for example the face, the device can further comprises an aperture 20 for any area for which iontophoretic treatment is not desired, for example, the bodily areas of the eyes, nose or mouth which is not a target surface for treatment. Such a device overcomes problems of how to treat a large area (such as the thigh) for example with a moisturizer or appearance modifying agent or with a dermatological agent or mild anesthetic or analgesic, particularly, when it is the face where the eyes, nose and/or month may need to be free of treatment or uncovered for comfort. The use of this device is not limited to the delivery of liposomes but can be used to deliver any substance conventionally known in the art for delivery by iontophoresis, for example, substances disclosed in U.S. Pat. No. 5,279,543, the disclosures of which are incorporated herein by reference.

Liposomes are vesicles composed of membrane-like lipid layers surrounding aqueous compartments. The lipid layers are made up mainly of phospholipids, which are amphophilic; they have a hydrophilic head and a lipophilic tail. In aqueous solution they are arranged into layers, which form closed vesicles, like artificial cells. A wide variety of conventional liposomes can be used with various numbers of lipid layers, size, surface charge, lipid composition.

Any of the known lipid or lipid like substances can be used in the present invention, both from natural or synthetic sources, including ceramides, lecithins, phosphatidyl ethanolamines, phosphatidyl serines, cardiniolipins, trilmoleins, phosphatidic acid and the like. The preparation of lipid vesicles is well known in the art, including U.S. Pat. Nos. 4,485,054; 4,761,288; 4,937,078 and "Liposome Technology," Vols. I, II and III (1984) G. Gregoriadis ed., CRC Press, Boca Raton, Fla. Any ionized substance/compound having a positive or negative charge and capable of being entrapped in or bound to the lipid vesicle by conventional methods known to those of skill in the art for entrapping and binding substances to lipid vesicles and otherwise inert to the material encapsulated for delivery to the patient can be included in the preparation of the lipid vesicle. Non-limiting examples of such substances with positive (+) charge include amines, such as stearylamine, and with negative (−) charge include, for example esters of inorganic acids, such as dicetyl phosphate, natural or synthetic lipids, such as phosphatidylserine, phosphatidylglycerol, phosphatidic acid, phosphatidylinositol, cardiolipin, and the like.

In one embodiment of the invention, the lipid vesicle is a multilamellar lipid vesicle (MLV) which is composed of a number of bimolecular lamellae interspersed with an aqueous medium.

In another embodiment of the invention, the lipid vesicle is a unilamellar vesicle which is composed of a single spherical lipid bilayer entrapping aqueous solution. In another embodiment of the method of the invention, the lipid vesicles are multivesicular that is composed of a number of vesicles.

In another embodiment of the method of the invention, the lipid vesicle composition comprises a multiphase composition comprising lipid vesicles (preferably multilamellar vesicles) encapsulating the substance, a saturated solution of the substance and the substance in solid form. The multiphase composition provides the substance to be administered in two states: in solid and in solution form within and outside the lipid vesicle and optimize the absorption and disposition of the substance. Accordingly, the method using multiphase vesicle compositions is particularly useful for compounds with low lipid or water solubility. By "low solubility" as used herein is meant that the solubility of the substance in water or lipid is too low for the substance to be practically administered in effective dose in conventional water or lipid formulations. Examples of such substances include retinoic acid, ampicillin, econazole base, econazole nitrate, amphotericin, diphenylhydantoin, minoxidil, methotrexate, lipophilic derivatives of muramyl dipeptide, acyclovir, interferon, ibuprofen, and the like. To prepare multiphase compositions, the substance is dissolved in the aqueous solution at a saturation level and is also present in the lipid film in a concentration higher than its lipid solubility. The lipid vesicle formation takes place at higher than room temperature from about 30 to about 95° C., so that the multiphase lipid vesicle compositions contain the substance in solution in both the aqueous and lipid phase in a saturated state and in crystalline or amorphous solid state.

Substances that can be transported into or through the tissue of a subject include any of a wide variety of cosmetic, diagnostic and biologically-active materials which can be encapsulated within a lipid vesicle. Some substances can have different uses depending on the circumstances and dose, for example, Vitamin E can be a nutrient or as an anti-aging antioxidant, some proteins, hormones and enzymes can be pharmaceuticals or diagnostic agents.

By "encapsulated" or "captured" is meant the capture of the substance by lipid vesicle in some way. This includes entrapment within the enclosed lipid bilayer either by fusing smaller vesicles around the substance or transmission through the membrane or forming the lipid vesicle within the solution containing the substance or incorporation into, or binding the substance to the lipid vesicles membrane itself. The substances can have varying degrees of lipophilicity.

By "biologically-active" as used herein is meant any substance which when present in an effective amount produces an effect in living cells or organisms, which includes pharmaceutically active substances.

As used herein "pharmaceutical" or "drug" means any chemical agent that affects or prevents processes in living organisms or cells. Non-limiting examples of drugs include those for therapy, prevention, diagnosis, and the like. It should be noted that some pharmaceutical agents, for example, estrogen, can also be considered as a cosmetic substances, depending on the circumstances and dose.

By "diagnostic agent" as used herein is meant any material that can be used to identify or locate a sign or symptom of a disease or condition in living cells or organisms.

As used herein "cosmetic" means any material used relating to appearance or adornment or for making beauty. While use of a cosmetic is primarily to the face, such use is not a limitation as cosmetics can be applied to other areas of the body such as hands, arms, legs, feet, abdomen and the like.

Examples of pharmaceutical compounds include those selected from the group consisting of dermatological agent, antibacterial agents, antifungal agent, anticonvulsant agents, antihypertensive agents, anticancer agents, immunomodulatory agents, antiviral agents, anesthetics, analgesics, tranquilizers, sedatives, muscle relaxants, non-steroidal anti-inflammatory agents and the like.

Non-limiting examples of cosmetics include vitamins, antioxidants, perfumes moisturizers, sunscreens, suntanning agents, and appearance modifying agents. Examples of cosmetics can be vitamin A, C, D or E, alpha-hydroxy acids such as pyruvic, lactic or glycolic acids, beta-hydroxy acids, caffeine, theobromine, lanolin, vaseline, aloe vera, methyl or propyl parban, pigments, dyes and the like for tattooing and make-up effects, estrogen, and other make-up agents, anti-aging agents, pigments such as iron oxide and titanium oxide) for uses after dermabrading of the skin for tattoo removal, iodine to reduce scar tissue, and the like.

Other substances include nutrients, DNA, RNA and the like.

Non-limiting examples of substances that can be administered by the method of the invention include steroids such as corticosteroids and -caine type compounds, such as lidocaine, in base form, estradiol, progesterone, demegestone, promegestone, testosterone, and their esters, nitro-compounds such as nitroglycerine, and isosorbide nitrates, nicotine, chlorpheniramine, terfenadine, triprolidine, hydrocortisone, oxicam derivatives such as piroxicam, ketoprofen, mucopolysaccharides such as thiomucase, buprenorphine, fentanyl, and its analogs, naloxone, codeine, dihydroergotamine, pizotiline, salbutamol, terbutaline, protaglandins such as misprostol and emprostil, omeprazole, imipramine, benzamides such as metaclopramide, scopolamine, peptides such as growth releasing factor, epidermal growth factor and somatostatin, cloidine, dihydroxypyridines such as nifedipine, verapamil, ephedrine, proanolol, metoprolol, spironolactone, thiazides such as hydrochlorothiazide, flunarizine, syndone imines such as molsiodmine, sulfated polysaccharides such as heparin fractions and salts of such compounds with physiologically acceptable acids and bases, penicillin and the like.

The substance encapsulated within the lipid vesicle can be administered in a physiologically acceptable carrier. Non-limiting examples of suitable physiologically acceptable carriers are well known in the art and include buffers, such as isotonic phosphate buffer saline (PBS), carriers for topical administration of pharmaceuticals and cosmetics including liquids, creams, oils, lotions, ointments, gels, solids, masks, make-up bases and the like.

In one embodiment of the invention, the multilamellar composition can be dispersed in a hydrocolloid, preferably by forming the multilamellar vesicles in the presence of an aqueous solution containing a hydrocolloid. By "hydrocolloid" or "hydrogel" or "gel" as used herein is meant any chemical substance which exhibits the ability to swell in water, retaining a significant amount of water within its structure and can be inorganic or organic, such as bentonite, methylcellulose or a single or polymer compound. The hydrocolloid effects the structure and inter-relation of the lipid vesicles and effect viscosity and adhesive properties of the final product and some can also effect the tissue itself.

If desired, one or more additional ingredients conventionally found in pharmaceutical or cosmetics can be included with the carrier, such as thickeners, preservatives, such as anti-oxidants, emulsifiers, dispersing agents, wetting agents, stabilizers, enzymes, and the like. Suitable additional ingredients, include, superoxide dismutase, stearyl alcohol, isopropyl mystriate sorbitan monooleate, polyethylene stearate, polyethylene glycol, water, alkali or alkaline earth lauryl sulfate, octyl dimethyl-p-amino benzoic acid, uric acid, reticulin, polymucosaccharides, hyaluronic acid, lecithin, polyethylene sorbitan monooleate, or any of the topical ingredients, disclosed in U.S. Pat. Nos. 4,340,586; 4,695,590; 4,959,353; 5,130,298; 4,761,288; 4,937,078; and 4,897,269, incorporated by reference.

While not required to practice the method of the invention, permeability enhancers conventionally known in the art can also be present, usually about 1 to about 10% by w. Suitable permeability enhancers include fatty acid esters and fatty alcohol ethers of $C_{1-4}$ alkanediols, alcohols such as ethanol, dimethyl sulfoxide, polyethylene glycol monolaurate and the like.

As one of skill in the art knows, the dose and frequency of administration of a substance by the method of the invention can vary depending on a number of factors, including the substance used, the intended use, potential skin irritation side effects, the lifetime of the substance, the tissue administered to, the age, sex and weight of the subject. Following the teachings of this application, one of skill in the art knows how to evaluate these factors and determine a suitable dose and frequency of administration. By way of non-limiting illustration, the substance being administered is present in the lipid versicle composition in an amount of about 0.0001% to about 10% by w, preferably from about 0.1% to about 5%.

EXAMPLES

The following examples are provided for illustration and should not be regarded as limiting the invention in any way.

Example 1

For the purpose of easy and reliable evaluation dyes and a local anesthetic agent were selected as model compounds. These ingredients were evaluated both in liposome-encapsulated (test) and in solution (control) forms. In each case the liposomal preparations contained a stearylamine, which provides a positive surface charge to the lipid vesicles.

| Liposomal Formula #1 | |
| --- | --- |
| Lecithin (Phospholipon 90-H) | 600 mg |
| Cholesterol | 125 mg |
| Stearylamine | 75 mg |
| Basic Fuchsin | 200 mg |
| Ethanol (95%) | 1.0 ml |
| Distilled water | 9.0 ml |
| Liposomal Formula #2 | |
| Lecithin (Phospholipon 90-H) | 500 mg |
| Stearylamine | 50 mg |
| Gentian Violet | 300 mg |
| Ethanol (95%) | 1.0 ml |
| Distilled water | 9.0 ml |
| Liposomal Formula #3 | |
| Lecithin (Phospholipon 90-H) | 1,000 mg |
| Stearylamine | 100 mg |
| Sudan III | 300 mg |
| Ethanol (95%) | 1.0 ml |
| Distilled water | 9.0 ml |
| Liposomal Formula #4 | |
| Lecithin (Phospholipon 90-H) | 1,000 mg |
| Stearylamine | 100 mg |
| Lidocaine (base) | 200 mg |
| Ethanol (95%) | 1.0 ml |
| Distilled water | 9.0 ml |

The above liposomal formulas were prepared according to the method described in U.S. Pat. No. 4,761,288. Control solutions of the above dyes (Formula No. 1 & 2) were prepared by using aqueous-alcoholic (10%) solution, and control preparation for Formulas No. 3 was made up by using 70% alcoholic solution. For Formula No. 4 we used a control which was also a liposomal preparation having the same chemical composition as the test product, except no stearylamine was present, therefore these lipid vesicles had a neutral net surface charge.

The penetration enhancement activity of the iontophoresis in case of Formulas 1, 2 and 3 was tested on rabbits ears, after the hair was shaved off. One ear was treated with the liposomal preparation, the other with the control, the solution form of the dye. Iontophoresis was carried out by using a Phoresor system with an electric current between 3–5 milliampere for 5–10 minutes. Since in the above examples the liposomes had a positive surface charge the positive (anode) electrode was placed over the test site to which 0.3 ml (either a liposomal, or solution) sample was applied with four layer of gauze pad. The negative (cathode) electrode was placed on the back of the rabbit and contained sodium nitrate solution as the return electrode. At the end of the experiment, the test areas were washed with alcoholic swabs.

Gross examinations indicated that the color on the liposome-treated areas were visible for a period of three-four weeks, while no color spot was visible any of the control (solution)-treated areas within three-four days.

Biopsy samples were taken from the liposome and control-treated areas after 3–4 weeks of the application. Microscopic examination of the skin sections treated with liposomes indicated some positive staining of the stratum corneum and of the epidermis, but the staining was much more positive within the dermis, particularly strong staining was observed at the hair follicles, which are located deep in the dermis. Microscopic evaluation of the control (solution)-treated areas produced negative results, i.e., no stains were noted in any section of the skin biopsies.

These results clearly demonstrated that the liposomes-encapsulated dyes penetrated into the skin and localized their content, i.e., the encapsulated dye mainly in the dermis, due to the positive surface charge of the liposomes and the positive electrode of the iontophoretic unit.

Example 2

Formula No. 4 was evaluated in human experiments. One arm of the volunteers was treated with the positive surface charged liposomes, and the other arm with the neutral surface charged liposomes of the lidocaine base (the drug was present in the un-ionized form, due to the alkaline pH of the preparation). The positive electrode was placed on the treated area, the negative electrode (containing sodium nitrate solution) was placed on the same arm approximately 30 cm away from the test site. One to three milliampere current was delivered for five minutes. The penetration enhancing activity of the iontophoresis was evaluated by the sensitivity to pin-prick, noting the time for the onset of action. Both liposomal preparations provided local anesthesia, but there was difference in the onset of action. In case of the positive surface charged liposome the onset of action was generally 10–20 minutes, while it was about 40–45 minutes in case of the neutral surface charged liposomes.

This result demonstrates that the penetration rate of the positive surface charged liposome was greater than the neutral surface charged liposomes, due to the effect of the positive electrode. The difference in the intensity of action due to the surface charge measured one hour after application was; the positive surface charged liposomes produced an activity of 5–7 painless score (out of ten pin pricks) the neutral surface liposomes provided 4–6 painless score.

While the examples have been illustrated using stearylamine to impart a positive charge to the liposome, one of skill in the art can following the teachings of this specification similarly use other positively or negatively charged substances, such as dicetyl phosphate, to produce other charged lipid vesicles.

What is claimed is:

1. A method for administration of an substance selected from the group consisting of an uncharged dye and uncharged anesthetic to a subject comprising applying directly to the skin or tissue of the subject a composition comprising said substance encapsulated within liposomes having either a positively or negatively charged surface by inotophoresis where the electric current is from about 1 to about 3 milliamperes and the duration is form about 1 to 15 minutes which causes dermal penetration.

2. The method of claim 1 wherein the composition contains multilamellar liposomes.

3. The method of claim 1 wherein the lipid vesicles comprise unilamellar liposomes.

4. The method of claim 1 wherein the liposomes are multivesicular.

5. The method of claim 2 wherein the multilamellar liposomes were formed in the presence of an aqueous solution containing a hydrocolloid gel.

6. The method of claim 1 wherein the uncharged anesthetic is lidocaine.

* * * * *